United States Patent [19]
Kim et al.

[11] Patent Number: 5,543,393
[45] Date of Patent: Aug. 6, 1996

[54] CYCLOSPORIN-CONTAINING POWDER COMPOSITION

[75] Inventors: Jung W. Kim, Seoul; Hee J. Shin; Joon K. Park, both of Kyeonggi-do; Kyeong B. Min, Seoul, all of Rep. of Korea

[73] Assignee: Chong Kun Dang Corp., Seoul, Rep. of Korea

[21] Appl. No.: 347,137

[22] Filed: Nov. 23, 1994

[30]    Foreign Application Priority Data

Feb. 25, 1994 [KR] Rep. of Korea .................. 94-3490

[51] Int. Cl.$^6$ ................... A61K 9/14; A61K 38/13; A61K 47/04
[52] U.S. Cl. .................. 514/11; 424/499; 514/9; 514/770; 514/970
[58] Field of Search .................. 424/491, 499; 514/770, 970, 9, 11; 530/317, 321; 930/270

[56]           References Cited

U.S. PATENT DOCUMENTS

| | | | |
|---|---|---|---|
| 4,388,307 | 6/1983 | Cavanak | 514/11 |
| 5,047,396 | 9/1991 | Orban et al. | 514/11 |
| 5,190,753 | 3/1993 | Behrens et al. | 514/9 |
| 5,350,741 | 9/1994 | Takada | 514/11 |
| 5,389,382 | 2/1995 | List et al. | 514/11 |

FOREIGN PATENT DOCUMENTS

| | | |
|---|---|---|
| 38029 | 2/1989 | Japan. |
| 2222770 | 3/1990 | United Kingdom. |
| 2230440 | 10/1990 | United Kingdom. |

OTHER PUBLICATIONS

Chem. Pharm. Bull. vol. 37, No. 9, issued 1989, Takada et al, "Enteric Solid Dispersion of Cyclosporin A . . . ", pp. 2542–2544.

Pharmaceutical Research, vol. 6, No. 11, pp. 958–960, 1989, Lorenz Hahn, et al., "Solid Surfactant Solutions of Active Ingredients in Sugar Esters".

International Journal of Pharmaceutics, vol. 92, pp. 197–202, 1993, P. C. Lerk, et al., "Application of Sucrose Laurate, A New Pharmaceutical Excipient, in Peroral Formulations of Cyclosporin A".

*Primary Examiner*—Jeffrey E. Russel
*Attorney, Agent, or Firm*—Oblon, Spivak, McClelland, Maier & Neustadt, P. C.

[57]           ABSTRACT

The present invention relates to a cyclosporin-containing powder composition which comprises cyclosporin, a non-ionic hydrophilic surfactant and a porous carrier. In addition, the present invention relates to a method for preparing the cyclosporin-containing powder composition which comprises dissolving cyclosporin and a non-ionic hydrophilic surfactant in an organic solvent, adding a porous carrier to the resulting solution and then evaporating the organic solvent from the mixture. The powder composition of the present invention is stable and does not require a special manufacturing technique when it is formulated. In addition, since the powder composition of the present invention does not contain an organic solvent, the necessity of a special package is excluded. Furthermore, the composition of the present invention provides an improved bioavailability which results in decrease of a single dosage, and therefore, can contribute to the alleviation of the side effects associated with cyclosporin.

12 Claims, 1 Drawing Sheet

CYCLOSPORIN-CONTAINING POWDER COMPOSITION

TECHNICAL FIELD

The present invention relates to a cyclosporin-containing powder composition. More particularly, the present invention relates to a cyclosporin-containing powder composition having an improved stability and an increased bioavailability, which contains cyclosporin, a non-ionic hydrophilic surfactant and a porous carrier. In addition, the present invention relates to a process for preparing the cyclosporin-containing powder composition.

BACKGROUND ART

Cyclosporin is a peptide compound having a unique structure consisting of 11 poly-N-methylated amino acids and has been known as having useful pharmacological activities, particularly immunosuppressive activity, antiinflammatory activity and the like. Cyclosporin compound which was first isolated from the natural product is ciclosporin as a spontaneous fungi metabolite, which is generally known as cyclosporin A and is the most widely used cyclosporin compound at the present time. Since cyclosporin A is first discovered, numerous cyclosporin compounds present in the natural world have been isolated and identified. At the present time they are prepared in industrial scale by a synthetic or semi-synthetic method or by a modified culture method.

Cyclosporin A has been recognized as having a very great value as an immunosuppressive agent in the clinical field. The effectiveness of cyclosporin A as the immuno-suppressive agent is demonstrated particularly in the field of organ transplantation, for example, transplantation of heart, lung, liver, kidney, pancreas, bone marrow, skin and cornea tissues. In addition, cyclosporin A is very useful for the treatment of autoimmune diseases and inflammatory conditions, particularly arthritis, for example, rheumatoid arthritis, chronic arthritis, progressive arthritis and arthritic malformation, and inflammatory conditions caused by autoimmune components such as rheumatic diseases.

However, in spite of the great effectiveness of cyclosporin in the field of organ transplantation and treatment of autoimmune diseases the clinical use of cyclosporin is very restricted because cyclosporin is very difficult to provide an effective and convenient administration method and has undesirable side effects such as serious nephrotoxicity. In addition, since cyclosporin is highly hydrophobic, it cannot be expected that the formulation prepared by a conventional method will provide an effective therapeutic effect.

In order to solve the above-mentioned problems related to cyclosporin U.S. Pat. No. 4,388,307 suggests a method for preparing a liquid formulation for internal use by mixing cyclosporin with Labrafil or Miglyol, ethanol and corn oil. However, such a liquid formulation should be administered as a dilution in potable water and is very difficult to provide the desired precise dosage for oral administration. Such problems involved in the liquid formulation could be solved by using a soft gelatin capsule formulation.

However, the cyclosporin soft gelatin capsule preparation has also a problem that ethanol as a solvent for cyclosporin should be used in a large amount in order to keep cyclosporin in the state of solution. Specifically, when ethanol, which has a low boiling point, is evaporated from the capsule preparation, cyclosporin is precipitated and the precipitated cyclosporin is substantially not absorbed in the living body. Accordingly, the reduced ethanol content due to evaporation during storage has a significant influence upon the effect of cyclosporin preparation. In order to avoid such problem the soft gelatin capsule should be packed in the closed space, or wrapped in a special packing material such as a sealing film foam package or an aluminum film foam package, to minimize the evaporation of ethanol from the soft capsule preparations. However, such special package contributes to the increase in the product volume and the production costs. Further, it has been reported that the stability of the soft capsule preparation wrapped in such special package reduces as the storage period is getting longer.

For example, Sandimun$^R$ which is presently commercially available in the form of a liquid preparation for internal use, an injectable preparation and a soft capsule preparation has also the above-mentioned problems. Specifically, the Sandimun liquid preparation has the disadvantages that it should be diluted with milk or juice before administration and thus is difficult to provide a precise dosage. The soft capsule preparation has also a problem in that when the ethanol content in soft capsules is varied, cyclosporin dissolved in ethanol is precipitated out to decrease the bioavailability thereof. In order to avoid such problem Sandimun preparation should be wrapped in a special packing material which results in the increase of the product volume and the production costs.

In order to solve the above-mentioned disadvantages of the prior art British Patent Publication No. 2222770A proposes a preparation containing cyclosporin as an active ingredient and particularly in the form of a microemulsion or a microemulsion preconcentrate. The composition of this patent includes (1) a hydrophilic phase, (2) a hydrophobic phase and (3) a surfactant. In this patent, a method of formulating the composition into a hard gelatin capsule preparation is also described. However, since the composition to be filled in the hard gelatin capsule is in the liquid form, the capsule should be sealed by using a special technique, i.e. Quali-seal technique.

In addition, Korean Laid-open Patent Publication No. 90-12625 discloses a cyclosporin galenic preparation comprising cyclosporin as an active ingredient, a fatty acid sugar monoester, and a diluent or a carrier. However, since the composition of this preparation is also in the liquid state such as solution or suspension, the hard gelatin capsule filled with the composition should be sealed by means of Quali-seal technique as in British Patent Publication No 2222770. In addition, when the composition is absorbed into a carrier to prepare the tablet formulation, it has also a disadvantage that the stability of tablet preparations is bad due to a high hygroscopic property of saccharose monolaurate L-1695 as the fatty acid sugar monoester [see Pharmaceutical Research, Vol. 6, No. 11, 1989, p958, "Solid Surfactant Solutions of Active Ingredients in Sugar Esters" and International Journal of Pharmaceutics, Vol. 92, 1993, p197, "Applications of sucrose laurate, a new pharmaceutical excipient, in peroral formulations of cyclosporin A"]. According to the above-mentioned papers, the fatty acid sugar monoester such as saccharose monolaurate L-1695 has a hygroscopic property, it should be treated under the drying condition. Thus, under the condition of 70% relative humidity the dry fine powder should be subjected to the subsequent procedure within 30 minutes after its preparation. Further, the fatty acid sugar monoester is unsuitable for the preparation of any formulation by a direct compression, due to its poor fluidity. For improving the high hygroscopic property of saccharose monolaurate this patent uses an additive such as Plasdon XL, Crosspovidone, etc., in a large amount. Thus, when the surfactant sensitive to water is used, the operation should be practiced under the condition of low humidity and the special package capable of excluding moisture is required to wrap the product. If the high hygroscopic surfactant such as saccharose monolaurate is used for preparing the powder formulation without such restricted condition, the surfactant absorbes the moisture to hydrolyse and therefore, the bioavailability of cyclosporin is lowered. Accordingly, it was practically impossible to prepare the cyclosporin powder formulation.

Meanwhile, Korean Laid-open Patent Publication No. 93-113 discloses a pharmaceutical composition containing cyclosporin as an active ingredient in a carrier medium comprising (1) 1,2-propyleneglycol, (2) a mixture of monoglyceride, diglyceride and triglyceride, and (3) a surfactant. However, this composition is substantially a microemulsion preconcentrate and therefore, has the same disadvantages as in British Patent Publication No. 2222770A. As other patent publications relating to the cyclosporin composition, Korean Patent Publication No. 93- 6430 discloses a method for solubilizing a sparingly soluble drug with liposome. However, this method is difficult to use in the industrial scale for mass production. In addition, since according to this method the phospholipid is used in an amount of 20 to 40 times the drug, the volume of a unit dosage form is too large and therefore, this method cannot be practically used for the preparation of cyclosporin formulations in the industry.

DISCLOSURE OF INVENTION

Thus, the present inventors have considered that the powder formulation of cyclosporin will provide the more increased stability and bioavailability of cyclosporin in comparison with the cyclosporin liquid formulation and therefore extensively studied to develope a method for preparing cyclosporin preparation in the form of a powder formulation using various surfactants and carriers. As a result thereof, we have identified that cyclosporin can be prepared in the form of a stable powder composition using a certain surfactant and carrier components and thus completed the present invention.

Accordingly, it is an object of the present invention to provide a cyclosporin-containing powder composition which comprises (1) cyclosporin as an active ingredient, (2) a non-ionic hydrophilic surfactant and (3) a porous carrier.

Further, it is another object of the present invention to provide a method for preparing a cyclosporin-containing powder composition which comprises dissolving cyclosporin and a non-ionic hydrophilic surfactant in an organic solvent, absorbing the resulting solution into a porous carrier and then evaporating the organic solvent.

Since the composition of the present invention is in the form of a solid powder, it is stable and does not require a special manufacturing technique when it is formulated. In addition, since the powder composition of the present invention does not contain any organic solvent, the necessity of a special package is excluded. Furthermore, the composition of the present invention provides an improved bioavailability of cyclosporin, which results in decrease of a single dosage, and therefore, can contribute to the alleviation of the side effects associated with cyclosporin.

BRIEF DESCRIPTION OF DRAWINGS

For a thorough understanding of the nature and objects of the invention, reference should be had to the following detailed description taken in connection with the accompanying drawing in which.

BEST MODE FOR CARRYING OUT THE INVENTION

Figure 1:
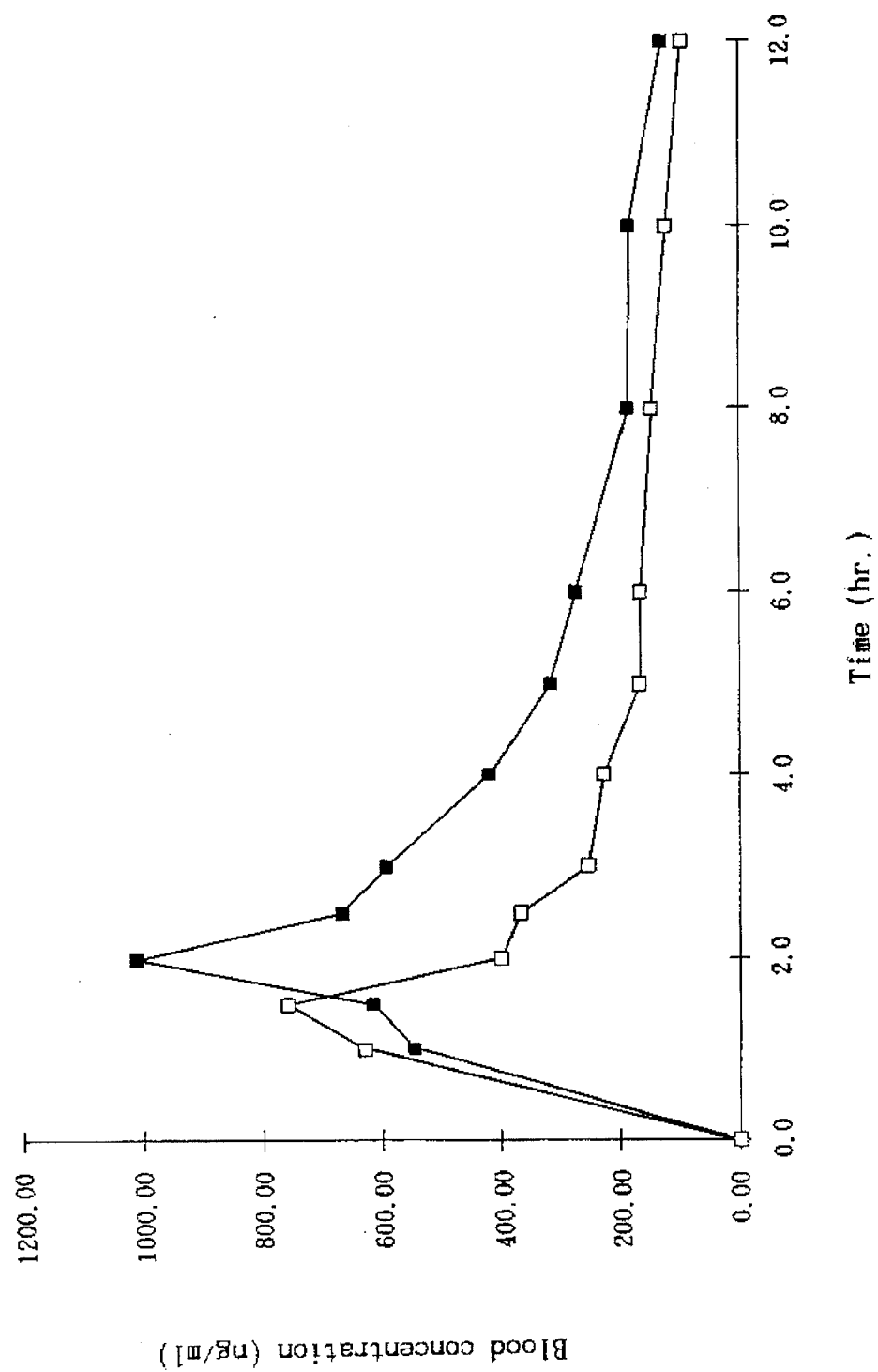
FIG. 1 is a graph showing the change in blood concentration over time after the composition according to the present invention. (composition I: ■—■) and a commercially available cyclosporin preparation (composition II: □—□) are orally administered.

In one aspect, the present invention relates to a cyclosporin-containing powder composition which comprises (1) cyclosporin as an active ingredient, (2) a non-ionic hydrophilic surfactant and (3) a porous carrier.

In another aspect, the present invention relates to a method for preparing a cyclosporin-containing powder composition which comprises dissolving cyclosporin and a non-ionic hydrophilic surfactant in an organic solvent, absorbing the resulting solution into a porous carrier and then evaporating the organic solvent to obtain the cyclosporin-containing powder composition in a white solid state.

Cyclosporin which is used as an active ingredient in the powder composition of the present invention is a cyclic peptide compound having useful immuonsuppressive activity and antiinflammatory activity as described above. Although cyclosporin A, B, C, D and G can be used as the cyclosporin component in the present invention, cyclosporin A is the most preferred one since its clinical effectiveness and pharmacological properties are well established in the art.

The non-ionic hydrophilic surfactant which is used as the second essential component in the powder composition according to the present invention can include, for example, the following components:

1. Polyethyleneglycol mono- and di-fatty acid ester, for example, polyethyleneglycol dicaprylate, polyethyleneglycol dilaurate, polyethyleneglycol hydroxystearate, polyethyleneglycol isostearate, polyethyleneglycol laurate, polyethyleneglycol ricinolate, polyethyleneglycol stearate, and the like, and more preferably polyethyleneglycol hydroxystearate which is commercially available as Solutol$^R$ HS15 (hydrogenation value=90–110, saponification value=53–63, acid value=maximum 1, water content= maximum 0.5%) and propyleneglycol capryl-capric acid diester which is commercially available as Myglyol$^R$ 840 (fatty acid content=$C_6$ maximum approximately 3%, $C_8$ approximately 65–80%, $C_{10}$ approximately 15–30%, $C_{12}$ maximum 3%, acid value=maximum 0.1, iodine value= approximately 320–340).

2. Reaction product of natural or hydrogenated vegetable oil, or polyoxyethylene glycolated natural or hydrogenated vegetable oil and preferably a product which is commercially available as Cremophor$^R$. The specific kinds of such Cremophor product include Cremophor RH40 (saponification value=approximately 50–60, acid value=maximum 1, iodine value=maximum 1, water content=maximum 2%, $n_D^{60}$=approximately 1.453–1,457, HLB=approximately 14–16), Cremophor RH60 (saponification value= approximately 40–50, acid value=maximum 1, iodine value=maximum 1, water content=approximately 4.5–5.5%, $n_D^{50}$=approximately 1.453–1.457, HLB=approximately 15–17) and Cremophor EL (molecular weight=approximately 1630 (measured by a steam osmometer), saponification value=approximately 65–70, acid value=approximately 2, iodine value=approximately 28–32, $n_D^{25}$=approximately 1.471). For this purpose, another suitable component is various products which are commercially available as Nikkol$^R$ preferably Nikkol HCL-60 (acid value=approximately 0.3, saponification value=approximately 47.4, hydroxylation value=approximately 42.5, pH (5%) =approximately 4.6, color APHA= about 40, melting point=about 36.0° C., freezing point= about 32.4° C., water content=approximately 0.03%).

3. Polyoxyethylene-sorbitan-fatty acid esters. This component is commercially available under the trade mark Tween$^R$ of which the specific example includes Tween 20 [polyoxyethylene(20) sorbitan monolaurate], Tween 40 [polyoxyethylene(20) sorbitan monopalmitate], Tween 60 [polyoxyethylene(20) sorbitan monostearate], Tween 80 [polyoxyethylene(20) sorbitan monooleate], Tween 65 [polyoxyethylene(20) sorbitan tristearate], Tween 85 [polyoxyethylen(20) sorbitan trioleate], Tween 21 [polyoxyethylene(4) sorbitan monolaurate], Tween 61 [polyoxyethylene(4) sorbitan stearate], Tween 81 [polyoxyethylene(5) sorbitan monooleate], and the like.

4. Polyoxyethylene-polyoxypropylene copolymers. This component is commercially available under the trade mark Emkalyx$^R$ and Pluronic$^R$. In the composition of the present invention Pluronic F68 is more preferably used.

5. Polyoxyethylene-polyoxypropylene block copolymers. This component is commmercially available under the trade mark Poloxamer$^R$. In the composition of the present invention Poloxamer 188 is more preferably used.

6. Polyoxyethylene fatty acid esters. This component is commercially available under the trade mark Cetiol$^R$ HE and Myri$^R$ of which the most preferable one is Myri 52 ($D^{25}$=approximately 1.1, melting point=approximately 40°–44° C., HLB=approximately 16.9, acid value=approximately 0–1, saponification value=approximately 25–35).

The porous carrier which is used as the third essential component in the composition of the present invention provides an advantage that a porocity of the carrier contributes to the increase in the surface area to increase the solubility. In addition, the porous carrier used in the present invention should satisfy the pharmaceutically acceptable general conditions that it does not cause any internal toxicity, has no antigenicity and is not accumulated in the body. Further, the carrier according to the present invention should have a stability to the impact during the processing procedures, a low solubility in organic solvent and an applicability to a human being, and should be suited for the condition depending on the desired administration routes.

Specific example of the porous carrier suitable for the present invention includes a water-soluble carrier such as sorbitol, sodium chloride, mannitol, lactose and the like. Since such carrier is completely dissolved within the human body, it contributes to the increase in bioavailability of cyclosporin. The most preferable one which can be used in the present invention is sorbitol.

In the composition of the present invention a water-insoluble carrier can also be used as the porous carrier. Specific example of the water-insoluble porous carrier includes micronized silicon dioxide or its alkylated compound, for example, the products commercially available under the trade mark Sylysia$^R$ and Aerosil$^R$. The most preferable one which can be used in the present invention is Sylysia 350 [average particle diameter=1.8 μm, loss on drying (950° C., 2 hours)=5%, pH(5% slurry)=approximately 7.5, whiteness degree=96, surface area=300 (m$^2$/g), oil absorption=310(ml/100 g), cavity volume=90 (ml/5 g)].

In the composition of the present invention the nonionic hydrophilic surfactant is used in the weight ratio of 1:1–20, preferably 1:2–15 and particularly preferably 1:3–10, with respect to cyclosporin as an active ingredient. In addition, the porous carrier is used in the weight ratio of 1:1–20, preferably 1:2–15 and particularly preferably 1:2–10, with respect to cyclosporin.

In the method for preparation of the composition according to the present invention, first cyclosporin and an non-ionic hydrophilic surfactant are dissolved in an organic solvent; the resulting solution is absorbed into a porous carrier; and the organic solvent is evaporated under reduced pressure from the absorbed carrier to obatin the solid product which can be then sieved to obtain a powder having the desired uniform size.

As the organic solvent in the method according to the present invention any low boiling solvent in which cyclosporin and the non-ionic hydrophilic surfactant can be dissolved can be used. Specific example of the solvent whcih can be used in the present invention includes methanol, ethanol, acetone, ether, chloroform, etc., of which any one solvent can be used alone or, if necessary, a mixture of two or more can also be used.

Although the cyclosporin-containing powder composition prepared according to the present invention can be used as it is prepared, it can also be used in the form of pharmaceutical preparation, for example, a solid formulation such as granule, tablet, hard capsule and the like, which is prepared using pharmaceutically acceptable conventional additives according to a conventional pharmaceutical method. In addition, the cyclosporin-containing powder composition of the present invention can be formulated in the form of a slow-released preparation. All of such cyclosporin preparations are included within the scope of the present invention.

The additive which can be used for this purpose includes a binder, a disintegrant, a lubricant, an excipient, a flavoring agent, a coloring agent, a taste corrective agent, and the like, which can be conventionally used in preparing the solid preparations.

The cyclosporin-containing powder composition, comprising the above-mentioned components, according to the present invention has advantages that since the composition is prepared in the form of a solid powder, it does not require any special condition and technique for their formulation in contrast to the prior preparations requiring a special technique such as Quali-Seal in their formualtion, and further the necessity of a special package is excluded because it does not contain any organic solvent. In addition, in the composition of the present invention the content of cyclosporin is stably maintained and therefore, the bioavailability of cyclosporin is increased in comparison with the prior art preparations. Accordingly, the composition of the present invention can allow to decrease the single dosage of cyclosporin and thus to reduce the occurrence of side effects. This can be a significant improvement since cyclosporin may cause a serious nephrotoxicity.

The present invention will be more specifically illustrated by the following examples. However, it should be understood that the present invention is not limited by these examples in any manner.

EXAMPLE 1 (Powder)

| Cyclosporin | 10 mg |
|---|---|
| Solutol HS15 | 500 mg |
| Sorbitol | 500 mg |
| Total | 1,100 mg |

500 mg of Solutol HS15 was dissolved in 1000 mg of ethanol and then 100 mg of cyclosporin was dissolved therein. The resulting solution was mixed with 500 mg of sorbitol having a particle size of 300 to 500 μm and the mixture was dried at 40° C. under reduced pressure to evaporate ethanol. 1100 mg of the obtained white solid was sieved to obtain the powder having a uniform particle size of 300 to 500 μm, which corresponds to the single dosage for 100 mg of cyclosporin.

EXAMPLE 2 (Powder)

| Cyclosporin | 100 mg |
|---|---|
| Cremophor RH40 | 600 mg |
| Sylysia 350 | 300 mg |
| Total | 1,000 mg |

The above-mentioned components were treated according to the same procedure as Example 1 to obtain a white powder preparation.

EXAMPLE 3 (Granule)

| Cyclosporin | 100 mg |
|---|---|
| Myglyol 840 | 450 mg |
| Sorbitol | 500 mg |
| Hydroxypropylmethylcellulose | 30 mg |
| Total | 1,080 mg |

Cyclosporin, Myglyol 840 and sorbitol were treated according to the same procedure as Example 1 to obtain a white powder which was then mixed with a solution of 30 mg of hydroxypropylmethylcellulose dissolved in 300 mg of distilled water to obtain the granule preparation.

EXAMPLE 4 (Granule).

| Cyclosporin | 100 mg |
|---|---|
| Cetiol HE | 450 mg |
| Sylysia 350 | 300 mg |
| Methylcellulose | 30 mg |
| Total | 880 mg |

The above-mentioned components were treated according to the same procedure as Example 3 to obtain the granule preparation.

EXAMPLE 5 (Tablet)

| Cyclosporin | 100 mg |
|---|---|
| Solutol HS15 | 500 mg |
| Sylysia 350 | 300 mg |
| Corn starch | 70 mg |
| Magnesium stearate | 7 mg |
| Total | 977 mg |

Cyclosporin, Solutol HS15 and Sylysia 350 were treated according to the same procedure as Example 1 to obtain the powder. Separately, 70 mg of corn starch was added to 1000 mg of distilled water and then heated to prepare the binder solution. The powder obtained above was mixed with the binder solution to prepare the granule which was then dried. The prepared granule was mixed with 7 mg of magnesium stearate and then the mixture was compressed to obtain a tablet containing 50 mg of cyclosporin per tablet.

EXAMPLE 6 (Tablet)

| Cyclosporin | 50 mg |
|---|---|
| Tween 80 | 50 mg |
| Myri 52 | 300 mg |
| Sorbitol | 250 mg |
| Hydroxypropylmethylcellulose | 90 mg |
| Magnesium stearate | 18 mg |
| Aerosil 200 | 9 mg |
| Total | 767 mg |

Cyclosporin, Tween 80, Myri 52 and sorbitol were treated according to the same procedure as Example 1 to obtain the powder which was then mixed with a solution of hydroxypropylmethylcellulose dissolved in 250 mg of the mixture of methanol and methylene chloride to prepare the granule. The prepared granule was dried and mixed with 18 mg of magnesium stearate and 9 mg of Aerosil 200 and then the mixture was compressed to obtain a tablet containing 50 mg of cyclosporin per tablet.

EXAMPLE 7 (Tablet)

| Cyclosporin | 100 mg |
|---|---|
| Cremophor RH40 | 600 mg |
| Sorbitol | 350 mg |
| Hydroxypropylmethylcellulose | 75 mg |
| Magnesium stearate | 30 mg |
| Total | 1,155 mg |

The above-mentioned components were treated according to the same procedure as Example 6 to obtain the tablet preparation.

EXAMPLE 8 (Hard gelatin capsule)

| Cyclosporin | 50 mg |
|---|---|
| Pluronic F68 | 200 mg |
| Myglyol 840 | 100 mg |
| Sylysia 350 | 250 mg |
| Methylcellulose | 25 mg |
| Total | 625 mg |

The above-mentioned components were treated according to the same procedure as Example 4 to obtain the granule which was then filled in a hard gelatin capsule to obtain the capsule preparation.

EXAMPLE 9 (Hard gelatin capsule)

| | |
|---|---|
| Cyclosporin | 50 mg |
| Poloxamer 188 | 300 mg |
| Soritol | 350 mg |
| Total | 700 mg |

The above-mentioned components were treated according to the same procedure as Example 1 to obtain the powder which was then filled in a hard gelatin capsule to obtain the capsule preparation.

EXAMPLE 10 (Hard gelatin capsule)

| | |
|---|---|
| Cyclosporin | 50 mg |
| Solutol HS15 | 150 mg |
| Cremophor RH60 | 200 mg |
| Sorbitol | 350 mg |
| Aerosil 200 | 17 mg |
| Total | 767 mg |

Cyclosporin, Solutol HS15, Cremophor RH60 and sorbitol were treated according to the same procedure as Example 1 to obtain the powder which was then mixed with Aerosil 200. The mixture was filled in a hard gelatin capsule to obtain the capsule preparation.

TEST EXAMPLE

Comparative test for bioavailability of the composition of the present invention and the commercial product in dogs The bioavailability of the composition according to the present invention was identified from the following experiment.

a) Test compositions
Composition I (composition of the present invention):

| | |
|---|---|
| Cyclosporin | 25 mg |
| Solutol HS15 | 250 mg |
| Sylysia 50 | 125 mg |
| Collidon CL | 8 mg |
| Total | 408 mg |

Composition II: SANDIMUN$^R$ 25 mg Soft capsule (Lot No. 114MFD1293)

b) Test procedure

In this experiment, 6 male dogs weighing 11.0–15.0 kg were used as the test animal. The test animal was fasted from 18 hours before administration of the test compositions, except that they are allowed to drink water. The test compositions (4 capsules) corresponding to 100 mg of cyclosporin per dog was orally administered by compulsion to the test animal and then 50 ml of water was administered to each test animal. After 4 hours from administration of the test compositions the foodstuffs were administered to the test animal. In this test the test animals were divided into two groups in which each group consists of 3 dogs, and the experiment was practiced according to the cross-over test method.

Blood was collected form a juglar vein in an amount of 2 ml each time before administration of the test compositions and 1, 1.5, 2, 2.5, 3, 3.5, 4, 5, 6, 8, 10 and 12 hours after administration of the test compositions, and then stored at −18° C. According to a method disclosed in the literature (Pharmaceutical Research, Vol. 8, No. 4, 1991, p518), the blood was pretreated with an organic solvent and then analyzed by means of HPLC [solvent: $CH_3CN$/pH 2.5 buffer solution/methanol=50/45/5, column: Lichrosorb RP-8 (5 µm), wavelength: 215 nm, temperature: 70° C., flow rate: 2.0 ml/min.].

C) Result

As the result of administration of two test compositions to 6 dogs according to the above-mentioned test procedure, AUC (ng.hr/ml) and blood concentration of cyclosporin in each group were described in the following Tables 1 and 2 and also depicted in FIG. 1.

TABLE 1

AUC (ng · hr/ml) after oral administration of the composition of the present invention and the commercial product

| | Composition I | Composition II |
|---|---|---|
| A | 3305.05 | 3016.43 |
| B | 3487.46 | 2910.20 |
| C | 2979.27 | 1614.13 |
| D | 6948.64 | 3244.72 |
| E | 3448.35 | 2354.94 |
| F | 6358.45 | 3166.61 |
| Average | 4421.20 | 2717.84 |

TABLE 2

Blood concentration (ng/ml) of cyclosporin after oral administration of the composition of the present invention and the commercial product

| Time (hr) | Composition I | Composition II |
|---|---|---|
| 0.0 | 0.00 | 0.00 |
| 1.0 | 546.96 | 629.12 |
| 1.5 | 617.35 | 759.46 |
| 2.0 | 1013.82 | 399.60 |
| 2.5 | 668.41 | 369.04 |
| 3.0 | 592.74 | 254.22 |
| 4.0 | 421.03 | 228.50 |
| 5.0 | 317.38 | 167.87 |
| 6.0 | 275.43 | 167.63 |
| 8.0 | 187.99 | 148.06 |
| 10.0 | 185.46 | 124.81 |
| 12.0 | 130.73 | 97.75 |

As can be seen from the result shown in the above tables and figure, the composition of the present invention shows an increase in the bioavailability by about 62% in comparison with the composition II as the commercial product. In addition, in view of the fact that the blood concentration of cyclosporin is maintained at 250 ng/ml or more by administration of the composition of the present invention, the duration of an effective blood concentration of about 250 ng/ml following to administration of the composition of the present invention is about two times that of the commercial product.

Although this invention has been described in its preferred form with a certain degree of particularity, it is appreciated by those skilled in the art that he present disclosure of the preferred form has been made only by way of example and that numerous changes in the details of the construction, combination and arrangement of parts may be resorted to without departing from the spirit and scope of the invention.

What is claimed is:

1. A cyclosporin-containing powder composition which comprises (1) cyclosporin, (2) a non-ionic hydrophilic surfactant and (3) a porous water-insoluble carrier selected from the group consisting of micronized silicon dioxide and alkylated micronized silicon dioxide.

2. The cyclosporin-containing powder composition of claim 1, characterized in that said cyclosporin is cyclosporin A.

3. The cyclosporin-containing powder composition of claim 1, characterized in that the non-ionic hydrophilic surfactant is selected from the group consisting of: polyethyleneglycol mono- and di-fatty acid esters, the reaction products of natural or hydrogenated vegetable oil, polyoxyethylene-sorbitan-fatty acid esters, polyoxyethylene-polyoxypropylene copolymers, polyoxyethylene-polyoxypropylene block copolymers and polyoxyethylene fatty acid esters.

4. The cyclosporin-containing powder composition of claim 3, characterized in that the non-ionic hydrophilic surfactant is polyethyleneglycol mono- or di-fatty acid esters.

5. The cyclosporin-containing powder composition of claim 4, characterized in that the non-ionic hydrophilic surfactant is polyethyleneglycol hydroxystearate.

6. The cyclosporin-containing powder composition of claim 1, characterized in that the carrier is Sylysia.

7. The cyclosporin-containing powder composition of claim 1, characterized in that the ratio of cyclosporin to non-ionic hydrophilic surfactant is 1:1–20 (w/w).

8. The cyclosporin-containing powder composition of claim 7, characterized in that the ratio of cyclosporin to non-ionic hydrophilic surfactant is 1:3–10 (w/w).

9. The cyclosporin-containing powder composition of claim 1, characterized in that the ratio of cyclosporin to porous water-insoluble carrier is 1:1–20 (w/w).

10. The cyclosporin-containing powder composition of claim 9, characterized in that the ratio of cyclosporin to porous water-insoluble carrier is 1:2–10 (w/w).

11. The cyclosporin-containing powder composition of claim 1, characterized in that the composition is formulated into a granule, tablet or hard gelatin capsule.

12. The cyclosporin-containing powder composition of claim 3, wherein said reaction product of natural or hydrogenated vegetable oil is polyoxyethylene glycolated natural or hydrogenated vegetable oil.

* * * * *